United States Patent [19]

Wool

[11] Patent Number: 4,479,779

[45] Date of Patent: Oct. 30, 1984

[54] ORTHODONTIC ARCH WIRE

[76] Inventor: Arthur L. Wool, 1402 Penn Ave., Wyomissing, Pa. 19610

[21] Appl. No.: 537,742

[22] Filed: Sep. 30, 1983

[51] Int. Cl.³ .............................................. A61C 7/00
[52] U.S. Cl. ...................................................... 433/20
[58] Field of Search ..................................... 433/20, 7

[56] References Cited

U.S. PATENT DOCUMENTS 1,014,028  1/1912  Angle .................................... 433/30
1,103,606  7/1914  Montag ................................. 433/20

Primary Examiner—Robert Peshock

Attorney, Agent, or Firm—Howson and Howson

[57] ABSTRACT

An arch wire for correction of anterior tooth malformations comprising a continuous, unitary, solid wire having circular cross-sections at least in its anterior segments and preferably throughout its length with the cross-sections of the anterior segments being smaller than the cross-sections of the posterior segments. The narrow anterior segment is easy to install and comfortable to the patient, while the larger posterior segments are more stiff and less likely to damage the patient's gums or pull out of the buccal tubes on the patient's molars even when the parts of the wire adjacent to the bicuspids and canines are unsupported.

10 Claims, 5 Drawing Figures

ORTHODONTIC ARCH WIRE

BRIEF SUMMARY OF THE INVENTION

This invention relates to orthodontic appliances, and particularly to a novel arch wire for the correction of malformations of anterior teeth.

Crowding, overlapping, and misalignement of anterior teeth are usually corrected by the application of gentle correcting forces to the teeth by an arch wire which extends through slots in brackets secured to the teeth. The arch wire, or at least the segment of the arch wire which extends through the anterior tooth brackets, has a spring characteristic such that it tends to straighten itself out. In doing so, it progressively brings the teeth into proper alignment with one another. The orthodontist attaches brackets to the patient's teeth in appropriate positions on the teeth. Initially, however, the brackets are not aligned. That is, they may be displaced with respect to each other in the vertical direction, as well as in horizontal directions. Furthermore, the brackets may be initially tilted. The brackets move into alignment with one another during the course of correction. Brackets used for this purpose may be either of the edgewise type, or of the "light-wire" (Begg) type.

The arch wire used for correction of the above-described anterior tooth malformations is ordinarily a thin arch wire, typically about 0.012–0.014 inch in diameter. It fits into the slots of the brackets with some degree of play. During the course of treatment, it may be replaced with similar arch wires having different characteristics. The anterior teeth treated by this method include the central and lateral incisors, and may also include the canines in some cases. The posterior segments of the arch wire typically extend through buccal tubes secured to the patients first molars. In most cases, there is no connection to the bicuspids, and, in many cases, there may be no connection to the canines.

Comparatively thick conventional circular arch wires, for example arch wires having diameters of 0.020 inch, are usable in the above-described technique, but are insufficiently flexible, and therefore are difficult to install in the anterior tooth brackets. Furthermore, they tend to exert excessive pressure on the anterior teeth, and may cause discomfort to the patient. These comparatively thick arch wires, furthermore, tend not to retain their elastic recall as well as thin arch wires. Thus, they tend not to be as effective as thinner arch wires in correcting the conditions in question.

On the other hand, where thin arch wires are used, for example arch wires having diameters in vicinity of 0.012 inch, other problems may arise. If there is no attachment to the bicuspids, and particularly if there is no attachment to the canines, a considerable length of the arch wire, extending from the buccal tube to the nearest anterior tooth bracket, is unsupported. These unsupported lengths in thin arch wires tend to lose their desired shape by reason of the forces of mastication. When this occurs, the patient's gums may be damaged by the wire. Furthermore, thin wires having long unsupported portions, may be accidentally pulled out of their buccal tubes.

Twin arches or bimetric arches are available, and can be used for the purpose of correcting anterior tooth malformations. These arches have small-diameter anterior segments with circular cross sections. Hollow end tubing is attached to both ends of the anterior segment by pinching.

When it is desired to attach elastic to the end tubing, special hooks may be incorporated into the end tubing itself, or may be slid over the end tubing and held in place by pinching, by welding, or by other suitable techniques. It is not possible to form elastic-retaining loops in hollow end tubing, and therefore more expensive auxiliary attachments, such as hooks, must be used for the connection of elastic to the end tubing. It is not possible to form closing loops in end tubing. Offset bends can be made in end tubing, but end tubing has no spring qualities. Therefore, offset bends in end tubing cannot be used to effect translational movement of posterior teeth.

The principal object of this invention is to provide a simple solution to the foregoing problems, and more particularly to provide an orthodontic arch wire which is highly effective in correcting anterior tooth malformations, which is easy to install, comfortable for the patient and capable of retaining its elastic recall, which does not tend to lose its shape and damage the patient's gums, and which does not tend to disengage the buccal tube in which it is anchored. It is also an object of the invention to achieve any and all of the foregoing objects and advantages in an arch wire in which elastic loops and closing loops can be formed without difficulty, and in which offset bends useful for effecting translational movement of teeth can be made.

The arch wire in accordance with the invention has solid posterior and anterior segments which are unitary and continuous with each other. The transition between the posterior and anterior segments is in the vicinity of the canines, and the anterior segment is circular in cross-section, with the areas of the cross-sections of the anterior segment being smaller than the areas of the cross-sections of the posterior segments. The arch wire in accordance with the invention may be formed by swaging or grinding the intermediate part of a length of wire having a uniform cross-section, or it may alternatively be formed by drawing a length of wire having a uniform cross-section in such a way that an intermediate portion of the wire decreases in diameter. Suitable metallurgical treatments are applied following swaging, grinding or drawing to impart appropriate spring characteristics to the wire.

Various other objects and advantages of the invention will be apparent from the followings detailed description when read in conjunctions with the drawings.

DETAILED DESCRIPTION

Figure 1:
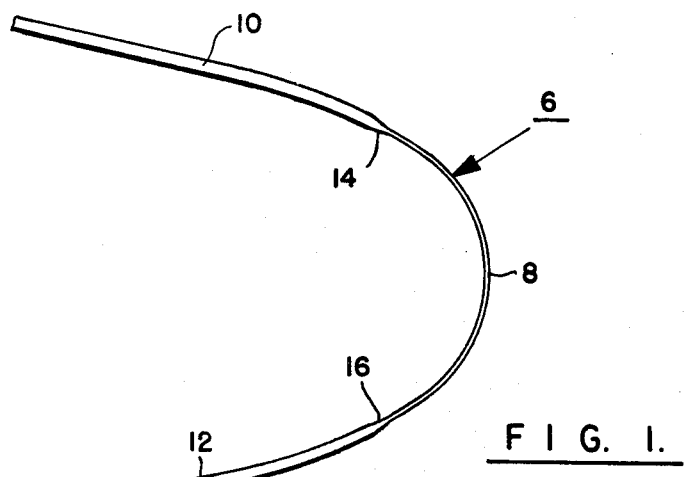
FIG. 1 is a plan view of a simple arch wire in accordance with the invention.

FIG. 1 shows a typical arch wire 6 in accordance with the invention comprising an anterior segment 8 and posterior segments 10 and 12. All three segments are unitary, i.e. they are formed from a single wire, and are in the form of a continuous arch, there being a transition at 14 between segments 10 and 8, and a transition at 16 between segments 8 and 12. All three segments are solid, i.e. their cross-sections are uniform, having no gaps or hollows.

The cross-section of anterior segment 8 is circular, and preferably the diameter of the anterior section is within the range of approximately 0.012 to 0.014 inches. The posterior segments are also preferably circular, although not necessarily so. If circular, their diameters are preferably within the range of approximately 0.018 to 0.020 inch. The anterior segments can have any of a variety of cross-sectional shapes. For example, the anterior segments could be in the form of "flat wires", having rectangular cross-sectional shapes. A typical flat wire cross-section is 0.011 inch horizonally and 0.022 inch vertically. In general, circular cross-sections are preferred for the posterior segments, because non-circular posterior segments are less easily formed with offset bends, elastic-retaining loops, closing loops and the like. In any case, the areas of the cross-sections of the anterior segments are smaller than the areas of the cross-sections of the posterior segments. That is, all parts of the anterior segments are small in cross-sectional area than the smallest part of the posterior segments. There may, of course be minor exceptions. For example, the anterior cross-sections may have torquing attachments, or the ends of the posterior segments may be tapered. Ordinarily, however, the cross-sections of any given segment will be uniform.

The transition points 14 and 16 of the arch wire of FIG. 1 are located in the vicinity of the canine, that is the vicinity where the canine should ideally be in a patient using the particular arch wire, and in any event neither invading the bracket position on an ideally positioned adjacent lateral incisor nor extending past the adjacent bicuspid.

Figure 2:
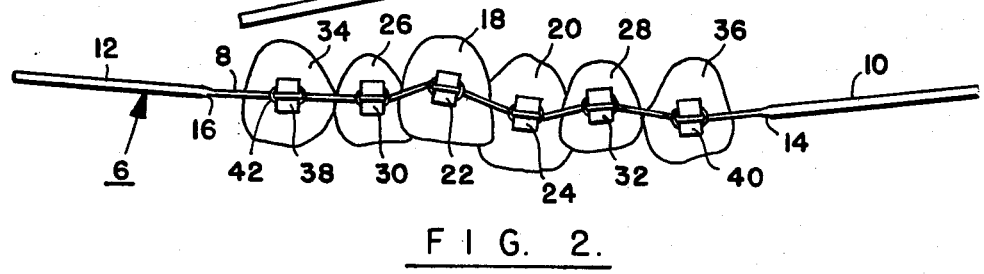
FIG. 2 is a planar development of a set of misaligned, crowded and overlapping anterior maxillary teeth, illustrating how an orthodontic appliance in accordance with the invention is attached to the teeth.

Arch wire 6 is shown in FIG. 2 attached by brackets to a set of anterior maxillary teeth, including the canines. The teeth are vertically misaligned, as well crowded and overlapping. Central incisors 18 and 20 are provided with brackets 22 and 24 respectively. Lateral incisors 26 and 28 are provided with brackets 30 and 32 respectively. Canines 34 and 36 are provided with brackets 38 and 40 respectively. These are edgewise brackets, and anterior segment 8 of the arch wire extends through generally horizontal slots in these brackets, and is secured therein by wire or elastic ligatures, one of which, on bracket 38, is indicated at 42.

There is a substantial vertical misalignment between incisor 18 and incisors 20 and 26. Accordingly, bracket 22 is positioned at a level higher than the levels of 30 and 24, and arch wire segment 8 extends upwardly from bracket 30 to bracket 22, and thence downwardly to bracket 24. As the arch wire tends to straighten itself by virtue of its elastic recall, a downward force is applied through bracket 22 to tooth 18, while corresponding upward forces are applied to teeth 20 and 26 through brackets 24 and 30 respectively. The direction and extent of vertical correction is controlled by inward positioning of the tooth brackets.

Tooth 18 also overlaps teeth 20 and 26, and therefore bracket 22 is forward of the locations of brackets 24 and 30. Arch wire segment 8 also applies a rearward force to tooth 18, and corresponding forward forces to teeth 20 and 26, these forces tending to correct the overlapping condition at least partially.

The tendency of the anterior arch wire segment 8 to straighten itself out also rotates teeth 18 and 22 counterclockwise and tooth 28 clockwise. The direction and extent of rotation is controlled by initial positioning of the tooth brackets.

In FIG. 2, it should be noted that transitions 14 and 16 are in vicinity of the canines, being located immediately to the sides of the adjacent bicuspids (not shown).

Figure 3:
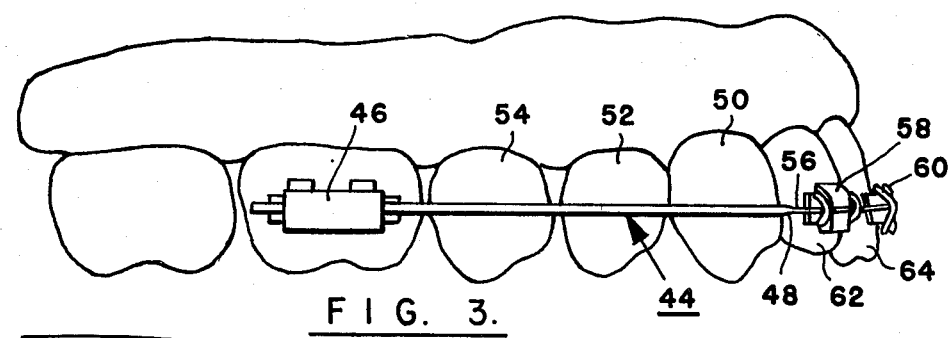
FIG. 3 is a side elevation of the maxillary teeth of a patient, showing an elongated unsupported part of an arch wire in accordance with the invention extending from a buccal tube on the right first molar to a bracket on the right lateral incisor.

FIG. 3 shows a similar arch wire 44 having a large diameter posterior segment and a small diameter anterior segment. The posterior segment extends through a conventional buccal tube 46 on the patient's first molar. The transition 48 between the posterior and anterior segments of the arch wire is located in the vicinity of canine 50, but toward the lateral incisor. In this case, canine 50 is not bracketed, and therefore the transition can be close to the bracket on the lateral incisor. Bicuspids 52 and 54 are also not bracketed, leaving a substantial unsupported length of wire between the buccal tube and bracket 58 on lateral incisor 62. When the canine is not bracketed, preferably a wire is chosen with its transition 48 toward the front of the canine, in order to insure that the unsupported part of the wire is of larger diameter throughout substantially its entire length. As shown in FIG. 3, the anterior segment 56 of the wire extends through edgewise brackets 58 and 60 respectively on incisors 62 and 64, and is secured to those brackets by ligatures.

The unsupported section of wire extending past bicuspids 52 and 54 and past canine 50, being of larger diameter, is less susceptible to deformation by mastication forces than a small diameter wire would be. Furthermore, it is less likely to become disengaged from buccal tube 46.

Figures 4, 5:
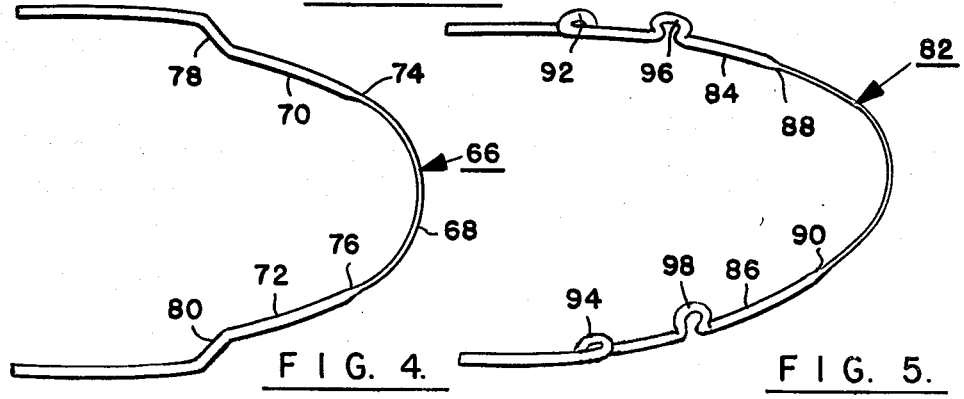
FIG. 4 is a plan view of an arch wire in accordance with the invention having lateral offset bends in its posterior segments.
FIG. 5 is a perspective view of an arch wire in accordance with the invention having both elastic loops and and closing loops in its posterior segments.

The posterior segments of the arch wire, being solid, can be bent in various ways, and can have spring qualities making them useful for effecting translational movement of the patient's posterior teeth. In FIG. 4, arch wire 66 comprises an anterior segment 68 and posterior segments 70 and 72, transitions being located at 74 and 76. The posterior segments are offset outwardly at 78 and 80. These lateral offset bends can be easily formed in circular wire or in wire having a rectangular cross-section. Vertical offsets can be formed in circular wire of solid cross-section, but may not be so easily formed in wire having a rectangular cross-section particularly where the wire is of the "flat-wire" configuration. Thus, the posterior segments of the wire are preferably circular in cross-section, so that they can be bent in various ways to form offsets or loops.

Arch wire 82 in FIG. 5 has posterior segments 84 and 86 extending rearwardly respectiveiy from transitions 88 and 90. The posterior segments are circular in cross-section. Elastic-retaining loops are formed in both of them at 92 and 94. Conventional closing loops are formed in the posterior segments at 96 and 98.

The arch wire in accordance with the invention has, as its principal advantage, its ability to correct various anterior tooth malformations without the need for support by connection through brackets to the patient's bicuspids. The arch wire has, as a further advantage, the fact that its posterior segments can be formed into loops and offsets for various purposes. This give the orthodontist a great deal of flexibility without requiring a large inventory of different styles of arch wire.

I claim:

1. An orthodontic arch wire having solid posterior segments having circular cross-sections and smooth surfaces allowing them to slide smoothly into buccal tubes, and a solid anterior segment of circular cross-section having a smaller diameter than that of the cross-sections of the posterior segments, the anterior and posterior segments being unitary and continuous, and the transition between the posterior and anterior segments being in the vicinity of the canines.

2. An orthodontic arch wire according to claim 1 in which the diameters of the cross-sections of the anterior segment are approximately within the range of 0.012 to 0.014 inch.

3. An orthodontic arch wire according to claim 1 in which the diameters of the cross-section of the posterior segments are approximately within the range of 0.018 to 0.020 inch.

4. An orthodontic arch wire according to claim 1 in which the diameters of the cross-sections of the anterior segment are approximately within the range of 0.012 to 0.014 inch and the diameters of the cross-section of the posterior segments are approximately within the range of 0.018 to 0.020 inch.

5. An orthodonic appliance according to claim 1 in which the posterior segments are bent to provide closing loops, elastic-retaining loops or offsets.

6. An orthodontic arch wire having solid posterior segments having smooth surfaces allowing them to slide smoothly into buccal tubes, and a solid anterior segment, the anterior and posterior segments being unitary and continuous, and the transition between the posterior and anterior segments being in the vicinity of the canines, the anterior segment being circular in cross-section and the areas of the cross-sections of the anterior segment being smaller than the areas of the cross-sections of the posterior segments.

7. An orthodontic appliance comprising a series of anterior brackets secured to anterior teeth of a patient, buccal tubes secured to posterior teeth of the patient on both sides of the mouth, and an orthodontic arch wire having solid posterior segments and a solid anterior segment, the anterior segment and posterior segments being unitary and continuous, and the transition between the posterior and anterior segments being in the vicinity of the canines, the anterior segment being circular in cross-section and the areas of the cross-sections of the anterior segment being smaller than the areas of the cross-sections of the posterior segments, the anterior segment extending through slots in the anterior brackets and being movable therein, and the posterior segments having smooth surfaces extending into said buccal tubes, the posterior segments being connected to posterior teeth solely through said buccal tubes.

8. An orthodontic appliance according to claim 7 in which the buccal tubes are secured to molars of the patient and in which the posterior segments extend past the ideal bicuspid locations in the patient's mouth.

9. An orthodontic appliance according to claim 8 in which the arch wire extends past the ideal canine locations in the patient's mouth without being connected to canines.

10. An orthodontic appliance according to claim 8 in which the posterior segments also extend past the ideal canine locations in the patient's mouth without being connected to canines.

* * * * *